United States Patent
Sekine

(10) Patent No.: US 11,790,154 B2
(45) Date of Patent: Oct. 17, 2023

(54) MOBILE TERMINAL DEVICE, SLIDE INFORMATION MANAGING SYSTEM, AND A CONTROL METHOD OF MOBILE TERMINAL

(71) Applicant: INTERACTIVE SOLUTIONS CORP., Tokyo (JP)

(72) Inventor: Kiyoshi Sekine, Tokyo (JP)

(73) Assignee: INTERACTIVE SOLUTIONS CORP., Tokyo (JP)

(*) Notice: Subject to any disclaimer, the term of this patent is extended or adjusted under 35 U.S.C. 154(b) by 1 day.

(21) Appl. No.: 17/232,673

(22) Filed: Apr. 16, 2021

(65) Prior Publication Data

US 2021/0232754 A1 Jul. 29, 2021

Related U.S. Application Data

(63) Continuation-in-part of application No. 14/655,964, filed as application No. PCT/JP2014/076960 on Oct. 8, 2014, now abandoned.

(30) Foreign Application Priority Data

Oct. 9, 2013 (JP) ................. 2013-212048

(51) Int. Cl.
*G06F 40/134* (2020.01)
*G06F 16/438* (2019.01)
(Continued)

(52) U.S. Cl.
CPC ........ *G06F 40/134* (2020.01); *G06F 16/4393* (2019.01); *G06F 40/106* (2020.01); *G06F 40/114* (2020.01); *G16H 15/00* (2018.01)

(58) Field of Classification Search
CPC .. G06F 40/134; G06F 16/4393; G06F 40/114; G06F 40/106; G16H 15/00
See application file for complete search history.

(56) References Cited

U.S. PATENT DOCUMENTS 5,859,623 A * 1/1999 Meyn ................. G06F 3/14
345/698
6,683,649 B1 1/2004 Anderson
(Continued)

FOREIGN PATENT DOCUMENTS

| JP | H07-49760 A | 2/1995 |
| JP | H08-171550 A | 7/1996 |

(Continued)

OTHER PUBLICATIONS

International Search Report of PCT/JP2014/076960 dated Nov. 18, 2014 [Disclosed in the parent U.S. Appl. No. 14/655,964 and therefore a copy of reference is not submitted herein].

(Continued)

*Primary Examiner* — Jeremy L Stanley
(74) *Attorney, Agent, or Firm* — Muncy, Geissler, Olds & Lowe, P.C.

(57) ABSTRACT

A mobile terminal device 20, comprising a display 21, wherein slide information to be displayed includes a plurality of pieces of the slide information independently stored as the slide information for each screen, the pieces of the slide information are configured to be able to be combined arbitrarily; the slide information includes main explanatory slide information for use in a main explanation, and relevant slide information as being the information in relation to the main explanatory slide information; and the slide information is configured to be able to be stored in association with the main explanatory slide information, and the display is configured to be able to display the main explanatory slide information associated with the relevant slide information by a transfer for one screen from the relevant slide information.

2 Claims, 12 Drawing Sheets

(51) Int. Cl.
  *G16H 15/00* (2018.01)
  *G06F 40/114* (2020.01)
  *G06F 40/106* (2020.01)

(56) References Cited

U.S. PATENT DOCUMENTS

| | | | | |
|---|---|---|---|---|
| 6,993,531 | B1* | 1/2006 | Naas | G06F 16/9562 |
| | | | | 707/999.102 |
| 7,051,019 | B1* | 5/2006 | Land | G06F 16/58 |
| | | | | 707/999.005 |
| 7,222,291 | B2* | 5/2007 | Estrada | G06F 40/174 |
| | | | | 715/201 |
| 7,299,418 | B2* | 11/2007 | Dieberger | G06F 3/04892 |
| | | | | 715/848 |
| 7,305,611 | B2* | 12/2007 | Coppin | G06F 40/10 |
| | | | | 715/201 |
| 7,330,875 | B1* | 2/2008 | Parasnis | H04L 65/612 |
| | | | | 709/227 |
| 7,373,605 | B2* | 5/2008 | Schaper | G06F 3/1431 |
| | | | | 715/761 |
| 7,380,211 | B2* | 5/2008 | Coulomb | G06F 40/169 |
| | | | | 715/730 |
| 7,526,726 | B1* | 4/2009 | Skwarecki | G11B 27/034 |
| | | | | 715/765 |
| 7,698,645 | B2* | 4/2010 | Fuse | G09B 5/067 |
| | | | | 715/730 |
| 7,702,522 | B1 | 4/2010 | Sholem | |
| 7,733,366 | B2* | 6/2010 | Beavers | H04L 12/1813 |
| | | | | 709/204 |
| 7,834,819 | B2* | 11/2010 | Dunn | G09B 5/02 |
| | | | | 715/761 |
| 7,941,412 | B2* | 5/2011 | Dunne | G06Q 50/18 |
| | | | | 707/694 |
| 7,958,147 | B1* | 6/2011 | Turner | G06Q 10/10 |
| | | | | 707/694 |
| 8,108,777 | B2 | 1/2012 | Penner | |
| 8,116,674 | B2 | 2/2012 | Matthews | |
| 8,166,010 | B2* | 4/2012 | Ives | G06F 16/9577 |
| | | | | 455/566 |
| 8,225,208 | B2* | 7/2012 | Sprang | G11B 27/34 |
| | | | | 715/730 |
| 8,281,245 | B1 | 10/2012 | Bennett | |
| 8,495,099 | B2 | 7/2013 | Maim | |
| 8,749,559 | B2* | 6/2014 | Maloney | G06T 13/20 |
| | | | | 345/473 |
| 8,875,008 | B2 | 10/2014 | Yuniardi | |
| 9,031,961 | B1 | 5/2015 | Cabanero | |
| 9,229,607 | B2* | 1/2016 | Powers | G06F 16/00 |
| 9,317,171 | B2* | 4/2016 | Chiu | G06F 3/048 |
| 9,335,904 | B2* | 5/2016 | Junqua | G16H 40/40 |
| 9,462,016 | B2* | 10/2016 | Huang | H04L 65/4038 |
| 9,477,380 | B2* | 10/2016 | Amijee | G06F 3/0482 |
| 9,619,128 | B2 | 4/2017 | Edge | |
| 9,626,068 | B2* | 4/2017 | Maloney | G06F 40/131 |
| 9,996,231 | B2* | 6/2018 | Missig | G06F 3/016 |
| 10,048,725 | B2* | 8/2018 | Boda | G06F 1/1645 |
| 10,127,944 | B2* | 11/2018 | Land | G11B 27/34 |
| 2001/0032125 | A1 | 10/2001 | Bhan | |
| 2002/0062228 | A1 | 5/2002 | Portnoy | |
| 2003/0048291 | A1* | 3/2003 | Dieberger | G06F 3/04892 |
| | | | | 715/732 |
| 2003/0101043 | A1 | 5/2003 | Boegelund | |
| 2003/0122863 | A1* | 7/2003 | Dieberger | G06F 3/0483 |
| | | | | 715/730 |
| 2003/0142145 | A1 | 7/2003 | Bennett, Jr. | |
| 2003/0174160 | A1 | 9/2003 | Deutscher | |
| 2003/0222900 | A1 | 12/2003 | Schramm-Apple | |
| 2004/0113934 | A1 | 6/2004 | Kleinman | |
| 2004/0194028 | A1 | 9/2004 | O'Brien | |
| 2005/0138570 | A1* | 6/2005 | Good | G06F 3/0481 |
| | | | | 715/788 |
| 2005/0149511 | A1 | 7/2005 | Ruthfield | |
| 2005/0197141 | A1* | 9/2005 | Jiang | G06F 16/955 |
| | | | | 455/457 |
| 2006/0067578 | A1 | 3/2006 | Fuse | |
| 2006/0074775 | A1 | 4/2006 | Roman | |
| 2006/0080610 | A1 | 4/2006 | Kaminsky | |
| 2006/0247968 | A1 | 11/2006 | Kadry | |
| 2006/0294046 | A1 | 12/2006 | Sareen | |
| 2006/0294468 | A1 | 12/2006 | Sareen | |
| 2006/0294469 | A1 | 12/2006 | Sareen | |
| 2007/0009872 | A1 | 1/2007 | Sonsteng | |
| 2007/0011616 | A1 | 1/2007 | Ording | |
| 2007/0112714 | A1 | 5/2007 | Fairweather | |
| 2007/0162953 | A1 | 7/2007 | Bolliger | |
| 2008/0077870 | A1 | 3/2008 | Napoleon | |
| 2008/0098018 | A1 | 4/2008 | King | |
| 2008/0288864 | A1 | 11/2008 | Qu | |
| 2010/0031152 | A1 | 2/2010 | Villaron | |
| 2010/0070448 | A1 | 3/2010 | Omoigui | |
| 2010/0088605 | A1 | 4/2010 | Livshin | |
| 2010/0091022 | A1 | 4/2010 | Shinohara | |
| 2010/0122171 | A1 | 5/2010 | Bauchot | |
| 2010/0257177 | A1 | 10/2010 | Yamamoto | |
| 2010/0309436 | A1 | 12/2010 | Allen, Jr | |
| 2011/0161821 | A1 | 6/2011 | Stewart | |
| 2011/0167351 | A1 | 7/2011 | Arora | |
| 2011/0196862 | A1 | 8/2011 | Bergman | |
| 2011/0311198 | A1 | 12/2011 | Tabe | |
| 2012/0084644 | A1 | 4/2012 | Robert | |
| 2012/0084656 | A1 | 4/2012 | Garroch | |
| 2012/0089621 | A1 | 4/2012 | Liu | |
| 2012/0095331 | A1 | 4/2012 | Ohashi | |
| 2012/0155828 | A1 | 6/2012 | Takahashi | |
| 2012/0284774 | A1 | 11/2012 | Vaughan | |
| 2012/0310994 | A1 | 12/2012 | Wionzek | |
| 2013/0101978 | A1 | 4/2013 | Ahl | |
| 2013/0194312 | A1 | 8/2013 | Yoshioka | |
| 2014/0010520 | A1 | 1/2014 | Bhatia | |
| 2014/0025650 | A1 | 1/2014 | Lee | |
| 2014/0152564 | A1 | 6/2014 | Gulezian | |
| 2014/0181650 | A1 | 6/2014 | Polubinski | |
| 2014/0282013 | A1* | 9/2014 | Amijee | G06F 3/0482 |
| | | | | 715/732 |
| 2014/0325362 | A1 | 10/2014 | Potts | |
| 2014/0331125 | A1 | 11/2014 | Tigchelaar | |
| 2015/0019591 | A1 | 1/2015 | Visscher | |
| 2015/0066868 | A1 | 3/2015 | Tanba | |
| 2015/0220688 | A1 | 8/2015 | Sasai | |
| 2015/0234800 | A1 | 8/2015 | Ehlen | |
| 2016/0086120 | A1 | 3/2016 | Powers | |
| 2016/0266864 | A1 | 9/2016 | Rajendran | |
| 2017/0011013 | A1 | 1/2017 | Tanaka | |
| 2017/0102912 | A1 | 4/2017 | Jambulingam | |
| 2017/0116179 | A1 | 4/2017 | Gagne-Langevin | |
| 2017/0123745 | A1 | 5/2017 | Sekine | |
| 2017/0200122 | A1 | 7/2017 | Edson | |

FOREIGN PATENT DOCUMENTS

| | | |
|---|---|---|
| JP | H09-204540 A | 8/1997 |
| JP | 2004-094853 A | 3/2004 |
| JP | 2005-275824 A | 10/2005 |
| JP | 2008-507776 A | 3/2008 |

OTHER PUBLICATIONS

Yusuke Aizawa, 'PowerPoint Skill Up Koza ( 10) Web no Yo na Slide Kose no Presentation', Myna vi News, Myna vi Corp., Jul. 12, 2013 (Jul. 12, 2013), [retrieval date Nov. 5, 2014 (Nov. 5, 2014)], Internet <URL: http://news.mynavi.ip/series/powerpoint/010/> and an original copy and partial translation of Written Opinion of the International Searching Authority for PCT/JP2014/076960 which includes partial translation of this Non Patent Literature [Disclosed in the parent U.S. Appl. No. 14/655,964 and therefore a copy of reference is not submitted herein].

Aizawa, Yusuke, "PowerPoint skill improvement lecture (10) The presentation of slide composition like Web", [online], Mynavi Corporation, Jul. 12, 2013, [the date of search Nov. 5, 2014], URL http://news.mynavi.jp/series/powerpoint/010/ (Cited in the office

(56) References Cited

OTHER PUBLICATIONS action of corresponding JP application No. 2013-212048 disclosed herein) (Disclosed in the parent U.S. Appl. No. 14/655,964 and therefore a copy of reference is not submitted herein).

"Can you maintain the hyperlink created by Word or Excel at the time of PDF conversion", [online], Adobe Systems, Aug. 6, 2008, [the date of search Nov. 5, 2014], URL http://kb2.adobe.com/jp/cps/478/4781.html (Reference that shows a well-known art) (Cited in the office action of corresponding JP application No. 2013-212048 disclosed herein) (Disclosed in the parent U.S. Appl. No. 14/655,964 and therefore a copy of reference is not submitted herein).

Office Action of the corresponding Japanese Patent Application No. 2013-212048 dated Jun. 14, 2017 and English machine translation thereof (Disclosed in the parent U.S. Appl. No. 14/655,964 and therefore a copy of reference is not submitted herein).

\* cited by examiner

31 STORAGE PORTION FOR EXPLANATORY MATERIALS FOR DOCTOR

32 STORAGE PORTION FOR EXPLANATORY SLIDE FOR DOCTOR α (EXPLANATORY SLIDES NOS. 1 TO 4, 11, 12, AND 21, AND THE DISPLAY ORDER THEREOF)

33 STORAGE PORTION FOR LITERATURE SLIDE FOR DOCTOR α (LITERATURE SLIDES NOS. 101 TO 108, 111, 112, AND 121, AND THE DISPLAY ORDER THEREOF)

34 STORAGE PORTION FOR EXPLANATORY MATERIAL-RELATED INFORMATION FOR DOCTOR α
"EXPLANATORY SLIDE NO. 3" → "REFERENCE GROUP 1 (LITERATURE SLIDES NOS. 101 TO 104)"
(LITERATURE SLIDES NOS. 105 TO 108), REFERENCE GROUP 2
"EXPLANATORY SLIDE NO. 11" → "REFERENCE GROUP (LITERATURE SLIDES NOS. 111 AND 112)"
"EXPLANATORY SLIDE NO. 21" → "REFERENCE GROUP (LITERATURE SLIDE NO. 121)"

35 STORAGE PORTION FOR EXPLANATORY SLIDE FOR DOCTOR β (EXPLANATORY SLIDES NOS. 11 TO 14 AND 21 TO 24, AND THE DISPLAY ORDER THEREOF)

36 STORAGE PORTION FOR LITERATURE SLIDE FOR DOCTOR β (LITERATURE SLIDES NOS. 111 TO 114, 121 TO 124, AND THE DISPLAY ORDER THEREOF)

37 STORAGE PORTION FOR EXPLANATORY MATERIAL-RELATED INFORMATION FOR DOCTOR β
"EXPLANATORY SLIDE NO. 11" → "REFERENCE GROUP (LITERATURE SLIDES NOS. 111 TO 114)"
"EXPLANATORY SLIDE NO. 21" → "REFERENCE GROUP (LITERATURE SLIDES NOS. 121 TO 124)"

MOBILE TERMINAL DEVICE, SLIDE INFORMATION MANAGING SYSTEM, AND A CONTROL METHOD OF MOBILE TERMINAL

CROSS REFERENCE TO RELATED APPLICATIONS

The present application is a continuation-in-part of U.S. patent application Ser. No. 14/655,964, filed on Jun. 26, 2015, which is a national stage application of PCT/JP2014/076960 filed on Oct. 8, 2014, and claims priority to Japanese Patent Application No. 2013-212048, filed on Oct. 9, 2013, and which are herein incorporated by reference.

TECHNICAL FIELD

The present invention relates to a mobile terminal device carried by, for example, a sales representative or the like, a slide information managing system, and a control method of a mobile terminal.

BACKGROUND FIELD

Conventionally, the mobile terminal device has been offered which supports sales activity of a sales representative (Patent Literature 1, for example).

Information provided to such a mobile terminal device is often provided by PDF ("Portable Document Format") or the like. This is because PDF or the like has the property that enables documents, images, or the like to be viewed in substantially unvaried state under all the environments without being influenced by a specific environment.

CONVENTIONAL ART DOCUMENTS

Patent Literature

Patent Literature 1: Japanese Patent Laid-Open Publication No. 2005-275824 (FIG. 1, etc.)

SUMMARY OF THE INVENTION

Problems to be Solved by the Invention

However, it take time to edit or the like materials created in PDF format, and thus it is difficult for a sales representative who is not specifically familiar with the format concerned to perform edits or the like.

For this reason, it has been very difficult in fact for each of sales representatives to create the most appropriate sales material for each customer of his/hers by editing the materials in PDF or the like, aside from the theory.

Then, if the materials are created so that sales representatives or the like do not need to perform edits beyond his/her ability, a large amount of effort is required to create the materials, and also the amount of data of the whole materials increases. There has thus been a problem in which this is not desirable in view of a mobile terminal device.

Furthermore, it is a commonly used technique that a screen is shifted from a main explanatory slide to a relevant literature at the time of simultaneously offering an explanation of relevant literatures or the like in relation to the explanation of slides such as PDF by means of a mobile terminal.

However, it is often difficult to transfer the screen to the previous explanatory slides after the relevant literatures are explained, and thus the unnecessary interval in the explanation is generated by that much. There has thus been a problem in which the explanation to a customer of a sales representative or the like becomes less effective.

For this reason, the object of the present invention is to provide a mobile terminal device in which a user such as a sales representative or the like can easily perform edits, the amount of data materials is not increased as a whole, and no unnecessary interval is generated during the explanation, thereby preventing the effect of the explanation by a user to a person of interest such as a customer from decreasing, a slide information managing system, and a control method of a mobile terminal.

Means for Solving the Problem

According to the present invention, the object described above is achieved by a mobile terminal device, comprising a display displaying various information, wherein slide information to be displayed on the display includes a plurality of pieces of the slide information independently stored as the slide information for each screen, the pieces of the slide information are configured to be able to be combined arbitrarily; the slide information includes main explanatory slide information for use in a main explanation, and relevant slide information as being the information in relation to the main explanatory slide information; and the slide information is configured to be able to be stored in association with the main explanatory slide information, and the display is configured to be able to display the main explanatory slide information associated with the relevant slide information by a transfer for one screen from the relevant slide information.

According to the configuration described above, it is configured so that slide information to be displayed on the display includes a plurality of pieces of the slide information to be independently stored as the slide information for each screen, and the pieces of the slide information are configured to be able to be combined arbitrarily.

For example, in the conventional slide information such as PDF, a plurality of PDF slides is formed as a certain unit of chunk, and is stored so that it is difficult to be separated into individual PDF slides. In this case, it is difficult for a user such as a sales representative to clip or the like a part of the PDF slides. If it is possible, a complicated operation has been required. Consequently, it has been difficult for each user to perform edits such as rearrangement of the order of PDF slides in accordance with each customer.

In this regard, in the configuration described above, the slide information includes a plurality of pieces of the slide information to be independently stored as the slide information for each screen, and the pieces of the slide information are configured to be able to be combined arbitrarily. Therefore, the user can easily perform edits of the slides or the like without the necessity of complicated operation.

Furthermore, according to the configuration described above, the slide information includes main explanatory slide information for use in a main explanation, and relevant slide information as being the information in relation to the main explanatory slide information, and the relevant slide information is configured to be able to be stored in association with the main explanatory slide.

Conventionally, it has been impossible to freely rearrange and establish the association of slides such as PDF. Therefore, when the slides such as PDF of main explanatory slide information are associated with the slides of the relevant slide information, it has been necessary to generate a set to which the slides of the relevant slide information for each slide of each main explanatory slide information, in every main explanatory slide information.

Consequently, when there is a plurality of main explanatory slides with which the same relevant slide information is associated, the same relevant slide information have to be associated with each main explanatory slide to generate the set thereof. As a result, the mobile terminal device has to store a plurality of the same pieces of relevant slide information or the like, and thus the amount of data has been increased.

In this regard, in the configuration described above, it is configured so that the slide information includes a plurality of pieces of the slide information independently stored as the slide information for each screen, the pieces of the slide information are configured to be able to be combined arbitrarily, and the relevant slide information can be stored in association with the main explanatory slide.

More specifically, in the configuration described above, it is not necessary to form the main explanatory slide information and the relevant slide information as being a set, and thus it is possible to achieve the configuration of one relevant slide information associated with a plurality of pieces of main explanatory slide information. The mobile terminal device thus is not required to store a plurality of the same pieces of relevant slide information, and thus the amount of data can be reduced by that much.

Furthermore, in the configuration described above, the display can display the main explanatory slide information associated with the relevant slide information by a transfer for one screen from the relevant slide information.

Consequently, a user can display the main explanatory slide information on the display, and then display the relevant slide information associated with the main explanatory slide information to offer an explanation, followed by promptly displaying the previous main explanatory slide information on the display.

Therefore, since no interval is generated in the transfer from the relevant slide information to the previous main explanatory slide information as in the conventional case, no unnecessary interval is generated at the time of explaining the main explanatory slide information. The explanation by a user to a person of interest such as a customer thus does not becomes less effective, and it is thus possible to offer an effective explanation.

Preferably, it is characterized in that the slide information includes a PDF ("Portable Document Format") format.

Preferably, it is characterized in that it is configured to be able to communicate with a slide information management device managing the slide information.

According to the present invention, the object described above is achieved by a control method of a mobile terminal device, wherein slide information to be displayed on the display displaying various information includes a plurality of pieces of the slide information independently stored as the slide information for each screen, the pieces of the slide information are configured to be able to be combined arbitrarily; the slide information includes main explanatory slide information for use in a main explanation, and relevant slide information as being the information in relation to the main explanatory slide information; and the slide information is configured to be able to be stored in association with the main explanatory slide information, and the display is configured to be able to display the main explanatory slide information associated with the relevant slide information by a transfer for one screen from the relevant slide information.

Advantages of the Invention

The present invention has the advantage of being capable of providing a mobile terminal device, a slide information managing system, and a control method of mobile terminal in which a user such as a sales representative can easily perform edits, the amount of data materials is not increased as a whole, and no unnecessary interval is generated during the explanation, thereby preventing the effect of the explanation by a user to a person of interest such as a customer from decreasing.

BRIEF DESCRIPTION OF THE DRAWINGS

FIG. 4 is a schematic block diagram showing a main configuration of a first various information storage portion in FIG. 3.

FIG. 13A is a view illustrating one explanatory slide. FIG. 13B is a view illustrating one literature slide.

DESCRIPTION OF EMBODIMENTS

Preferred embodiments of the present invention will be described below in detail with reference to the attached drawings.

In addition, the embodiments described below are preferred embodiments of the present invention, and thus include a variety of technically desirable limitation. The scope of the present invention, however, shall not be limited to those embodiments unless there is any description of limitation on the present invention in the explanation below.

Figure 1:
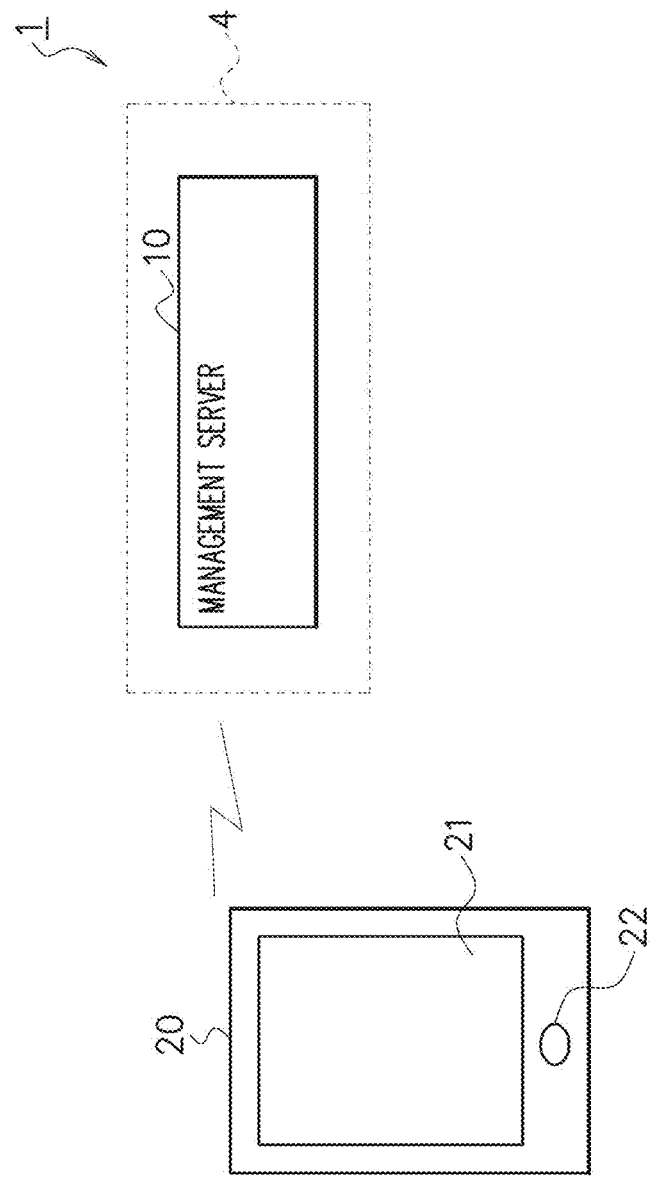
FIG. 1 is a schematic diagram showing a slide information managing system of the present invention, e.g., a managing system of explanatory materials for doctor.

FIG. 1 is a schematic diagram showing a slide information managing system of the present invention, e.g., a managing system of explanatory materials for doctor 1.

As shown in FIG. 1, the managing system of explanatory materials for doctor 1 has a management server 10, for example, which is an information management device for managing explanatory materials for doctors made with slide information such as PDF. The management server 10 is in possession of a pharmaceutical company 4, for example.

Furthermore, the system 1 has a tablet terminal 20, for example, which is a mobile terminal device. The tablet terminal 20 is the terminal which is held by each MR (medical representative) of the pharmaceutical company 4 for use in providing medical information while meeting doctors in a hospital or the like.

As shown in FIG. 1, the tablet terminal 20 has, at the center thereof, a "touch panel type display 21" having a vertical long rectangular shape. A touch panel is electronic equipment which is a combination of a display, e.g., a display, and a position input device, and also is an input device in which a user can input various information by touching an indication on the display.

Furthermore, the tablet terminal 20 has an input button 22 in addition to the touch panel type display 21.

In addition, as shown in FIG. 1, the tablet terminal 20 is configured to be able to communicate with the management server 10 which is managed by the pharmaceutical company 4.

The tablet terminal 20 and the management server 10 described above have a computer, and the computer has CPU (Central Processing Unit; not shown), RAM (Random Access Memory), and ROM (Read Only Memory) or the like which are connected to one another via a bus or the like.

Figure 2:
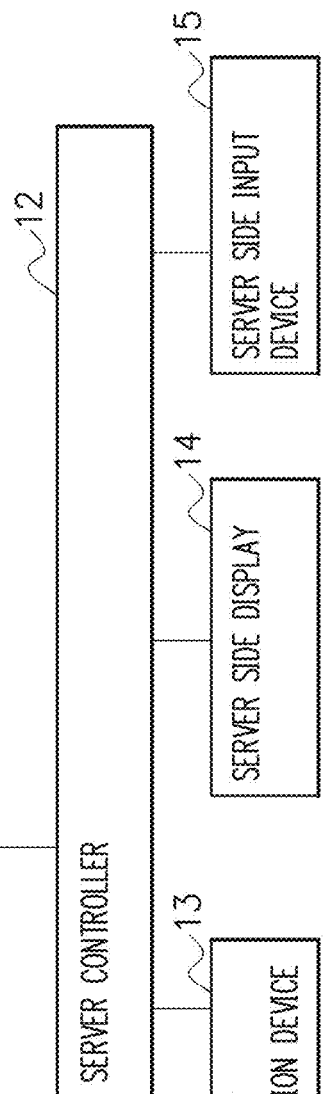
FIG. 2 is a schematic block diagram showing a main configuration of a management server in FIG. 1.

FIG. 2 is a schematic block diagram showing a main configuration of the management server 10 in FIG. 1. As shown in FIG. 2, the management server 10 has a "database of explanatory materials for doctor 11".

As shown in FIG. 2, the database of explanatory materials for doctor 11 has "explanatory material data for cardiovascular specialists", for example. The data concerned includes "Explanatory Slides Nos. 1 to 4" which are the main slide information constituted by, e.g., PDF or the like as "basic explanatory slide of high blood pressure".

Furthermore, as "relevant literatures of the basic explanatory slide", relevant slide information in relation to the explanatory slides Nos. 1 to 4, e.g., "Literature Slides Nos. 101 to 108" is included.

Furthermore, the database of explanatory materials for doctor 11 has "Explanatory Slides Nos. 11 to 14" as "explanatory slide of typical case such as a case of high blood pressure", and has "Literature Slides Nos. 111 to 114" as "relevant literature of explanatory slide of a typical case".

Furthermore, the database of explanatory materials for doctor 11 has "Explanatory Slides Nos. 21 to 24" as "typical therapeutic medicine explanatory slides for therapeutic medicine", and has "Literature Slides Nos. 121 to 124" as "relevant literature of typical therapeutic medicine explanatory slide".

Furthermore, the management server 10 has a "server controller 12". The server controller 12 is configured to control the database of explanatory materials for doctor 11, and also to control a "server side communication device 13" for communicating with the tablet terminal 20, a "server side display 14" displaying various information, and a "server side input device 15", as shown in FIG. 2.

Figure 3:
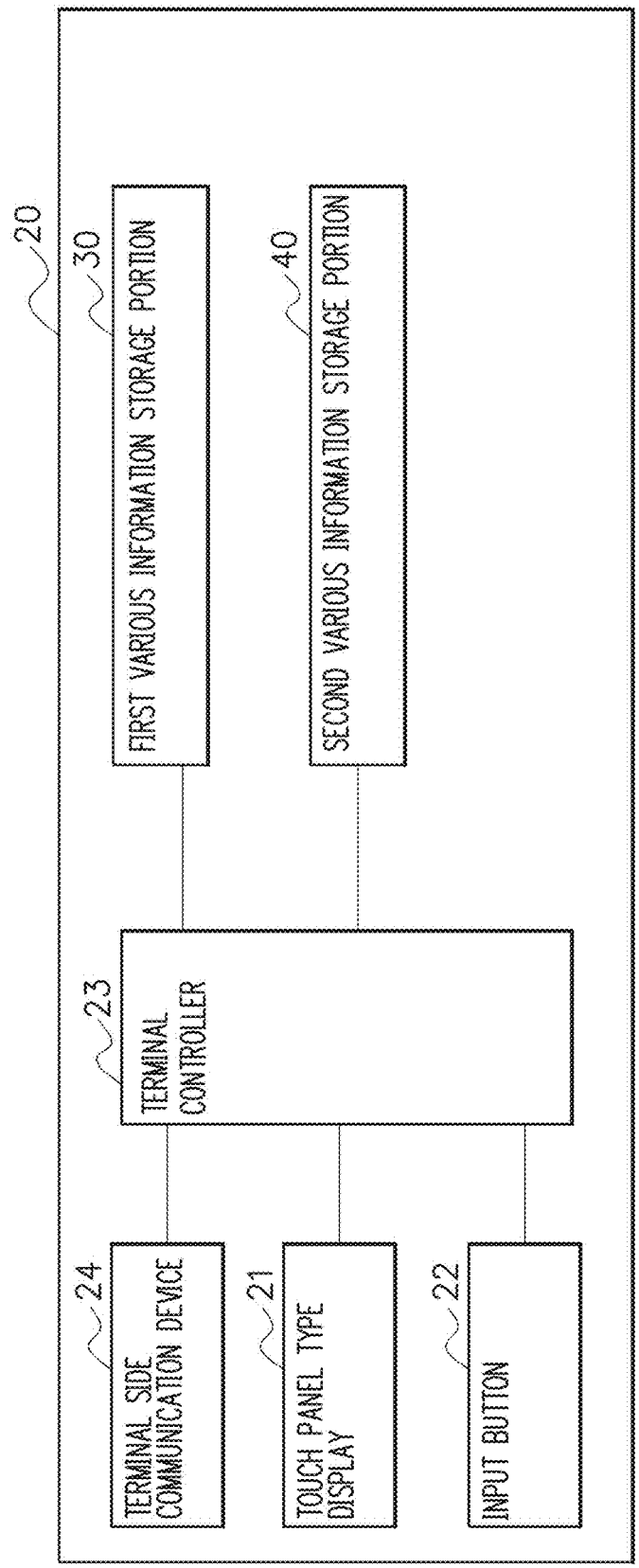
FIG. 3 is a schematic block diagram showing a main configuration of a tablet terminal shown in FIG. 1.

FIG. 3 is a schematic block diagram showing a main configuration of the tablet terminal 20 shown in FIG. 1.

As shown in FIG. 3, the tablet terminal 20 has a "terminal controller 23". The terminal controller 23 controls a "touch panel type display 21" and an "input button 22" shown in FIG. 1, as well as controls a "terminal side communication device 24" for communicating with the management server 10 in FIG. 1.

Furthermore, the terminal controller 23 also controls a "first various information storage portion 30" and a "second various information storage portion 40" shown in FIG. 3.

Figure 5:
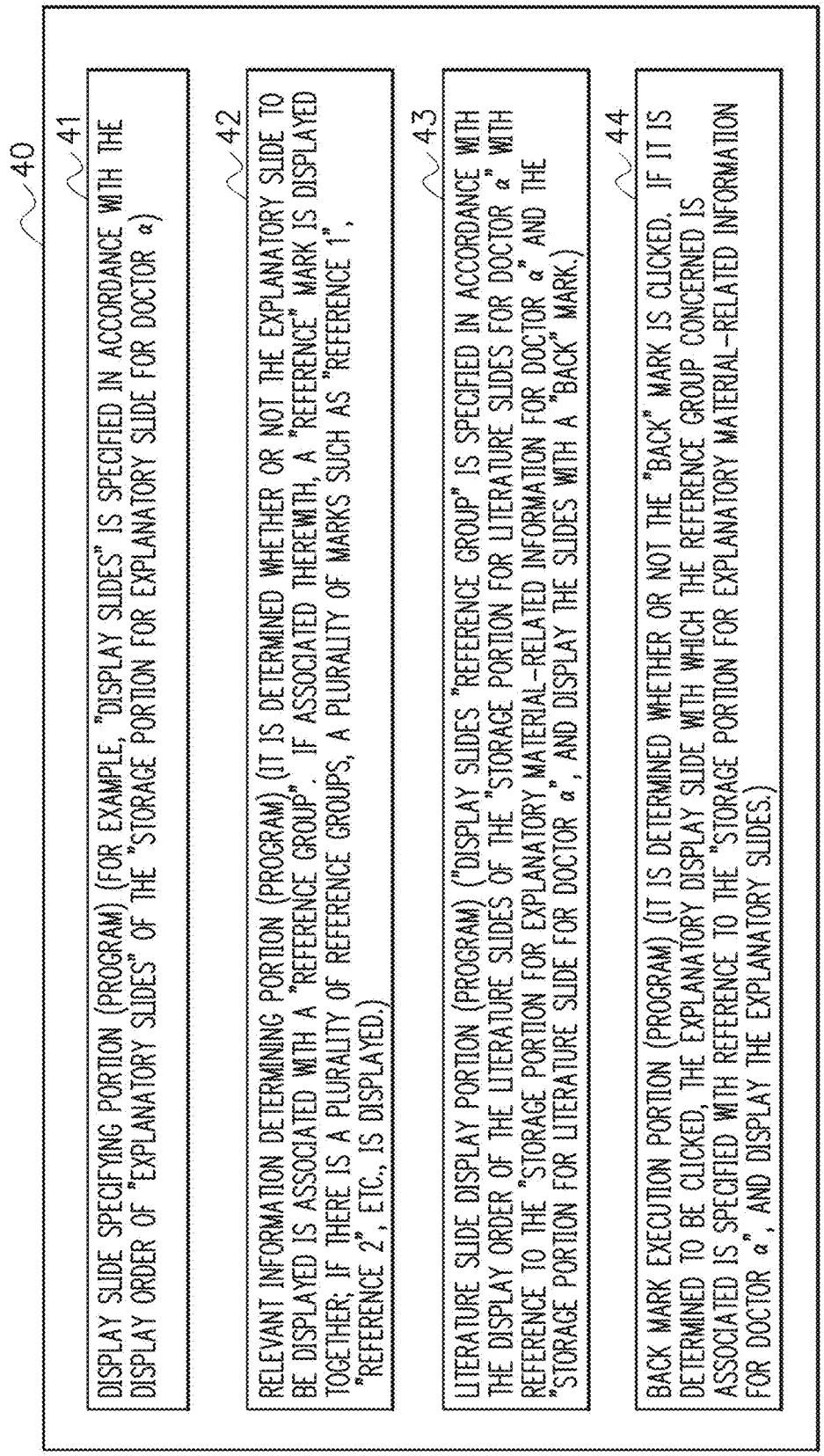
FIG. 5 is a schematic block diagram showing a main configuration of a second various information storage portion in FIG. 3.

FIGS. 4 and 5 are schematic block diagrams showing a main configuration of the first various information storage portion 30 and the second various information storage portion 40 in FIG. 3. The details thereof will be described later.

In the present embodiment, the description will be made below using the example of an MR (medical representative) of the pharmaceutical company 4 providing two doctors of cardiovascular department of a hospital (a doctor α and a doctor β) with medical information employing the tablet terminal 20 in FIG. 1.

Figure 6:
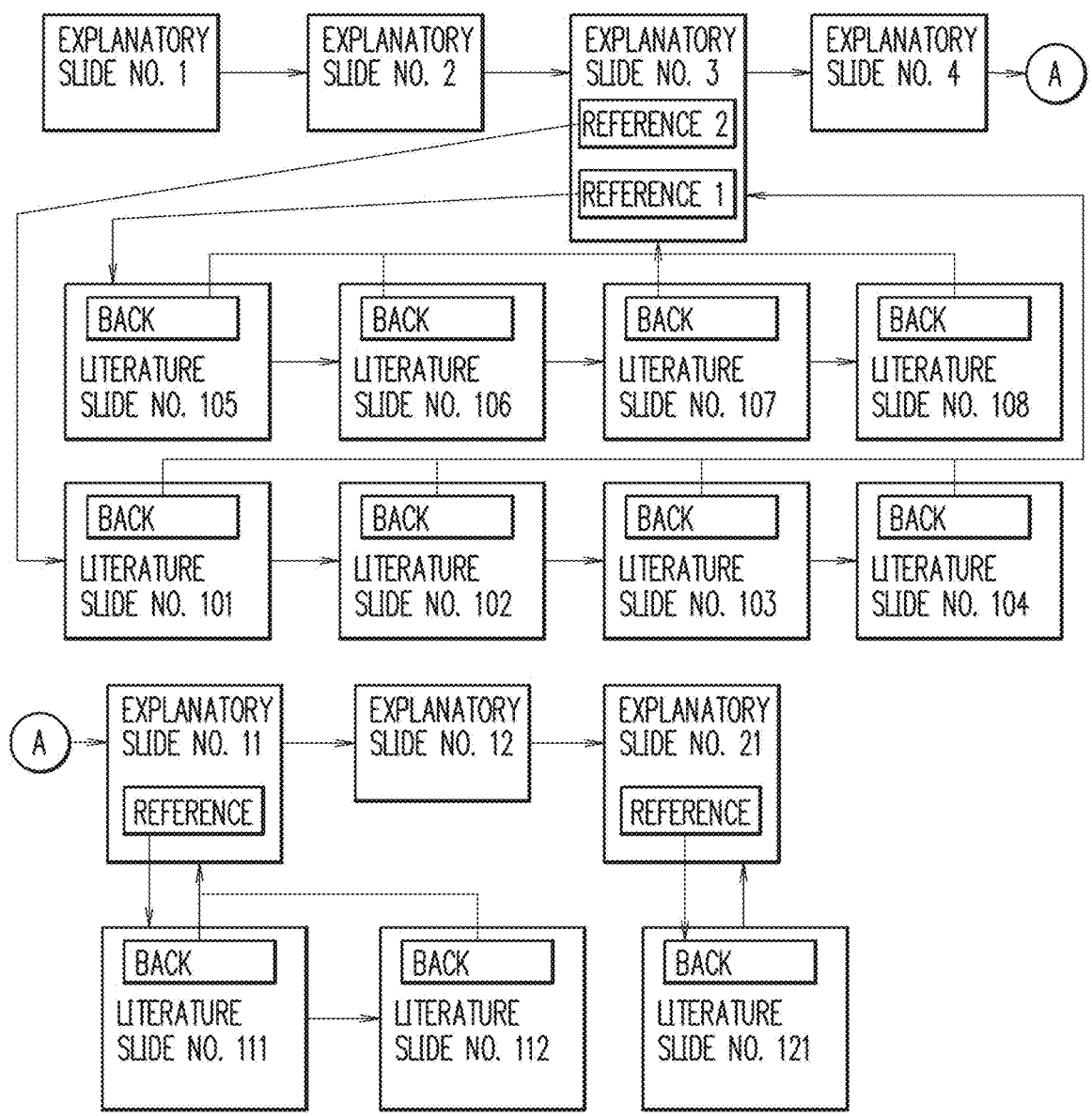
FIG. 6 is a schematic explanatory view showing a configuration of slides by which MR intends to offer an explanation to a doctor α.

FIG. 6 is a schematic explanatory view showing a configuration of slides by which the MR intends to offer an explanation to the doctor α. Since the doctor α is a resident, the explanation is configured to be made with an emphasis on relatively basic explanation.

More specifically, the MR has it in mind to display the slide information, e.g., slides as follows on the touch panel type display 21 of the tablet terminal 20.

Figure 7:
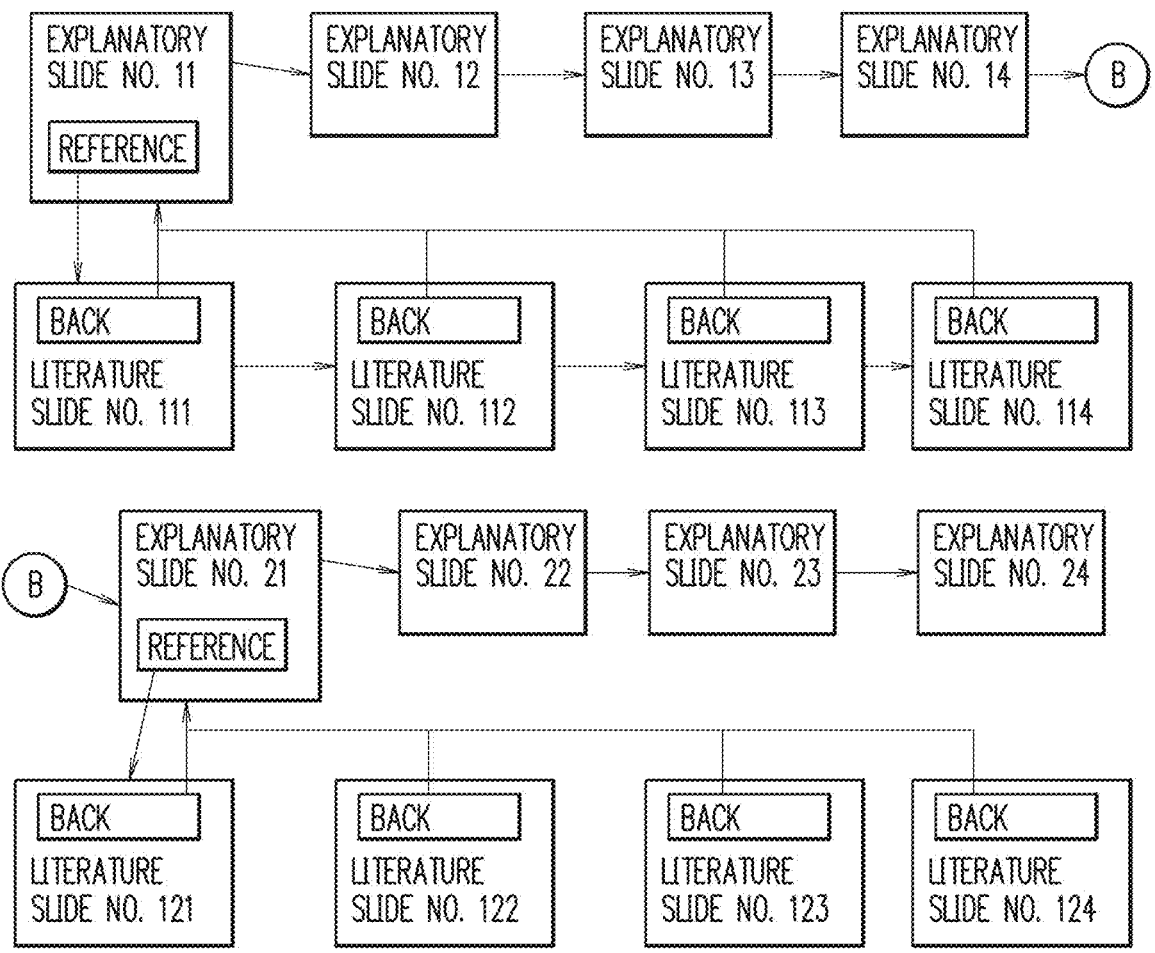
FIG. 7 is a schematic explanatory view showing a configuration of slides by which MR intends to offer an explanation to a doctor β.

FIG. 7 is a schematic explanatory view showing the configuration of slides by which the MR intends to offer an explanation to a doctor β. Since the doctor β is a head physician, the explanation is configured so that the basic explanation will be omitted and the emphasis is on the explanation of cases and therapeutic medicines.

FIGS. 8 to 12 are schematic flow charts showing the operational example of the managing system of explanatory materials for doctor 1.

Figure 8:
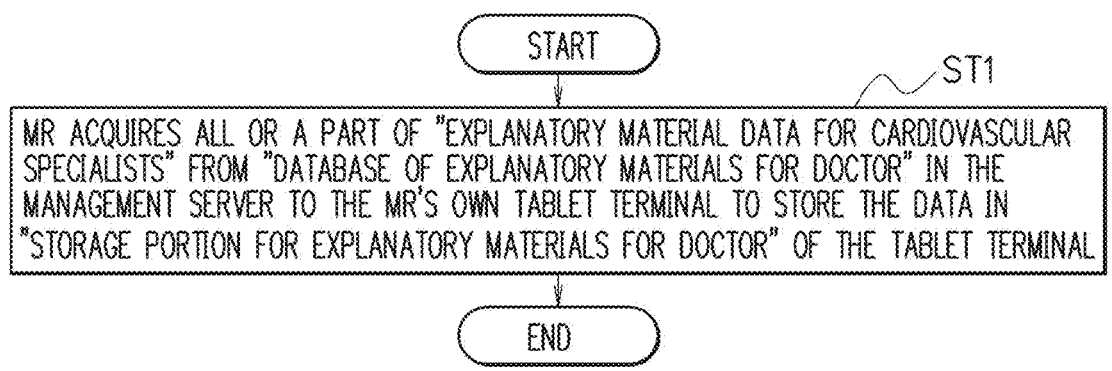
FIG. 8 is a schematic flow chart showing an operational example of a managing system of explanatory materials for doctor.

At step ST (hereinafter referred to as "ST") 1 in FIG. 8, the MR uses his/her own tablet terminal 20 in FIG. 1 to communicate with the management server 10. Then, all or a part of "explanatory material data for cardiovascular specialists" is acquired from a "database of explanatory materials for doctor 11" in the management server 10 to the MR's own tablet terminal 20 to store the data in a "storage portion for explanatory materials for doctor 31" of the tablet terminal 20 shown in FIG. 4.

Consequently, the tablet terminal 20 can subsequently create explanatory materials for each doctor offline without communicating with the management server 10, and display the information on the touch panel type display 21 to offer an explanation to each doctor. In this manner, since the explanation can be offered only by the tablet terminal 20 offline, the system is extremely easy to use.

Figure 9:
FIG. 9 is another schematic flow chart showing an operational example of the managing system of explanatory materials for doctor.

FIG. 9 is a schematic flow chart showing the steps of creating explanatory materials for doctor dedicated to the doctor α.

The MR executes at the steps in FIG. 9 the preparation of slides for the explanation shown in FIG. 6.

First, at ST11 in FIG. 9, explanatory slides Nos. 1 to 4, 11 to 14, and 21 to 24 such as PDF in the storage portion for explanatory materials for doctor 31 are selectively displayed on the touch panel type display 21 to select the necessary explanatory slides and the display order thereof.

For example, "Explanatory Slides Nos. 1 to 4, 11, 12, and 21" which are the explanatory slides to be used in FIG. 6 are selected and stored in a storage portion for explanatory slide for doctor α 32.

Then, the procedure proceeds to ST12. At ST12, "Literature Slides Nos. 101 to 108, 111 to 114, and 121 to 124" such as PDF in the storage portion for explanatory materials for doctor 31 are displayed on the touch panel type display 21 to select the necessary literature slides and the display order thereof.

For example, the literature slides Nos. 101 to 108, 111, 112, and 121 are selected to be displayed in this order, and are stored in a "literature slide storage portion for the doctor α 33".

Then, the procedure proceeds to ST13. At ST13, a group of literature slides associated with the explanatory slides of the storage portion for explanatory slide for doctor α 32 is designated and stored.

For example, in the case of FIG. 6, an explanatory slide No. 3, a reference group 1 (literature slides Nos. 105 to 108), and a reference group 2 (literature slides Nos. 101 to 104) are associated with one another, and stored in a "storage portion for explanatory material-related information for doctor α 34".

Furthermore, an explanatory slide No. 11 and a reference group (literature slide Nos. 111 and 112) are associated with each other, and also an explanatory slide No. 21 and a reference group (literature slide No. 121) are associated with each other, so as to store them in the storage portion for explanatory material-related information for doctor α 34.

In this manner, in the present embodiment, the explanatory slide and the literature slide are independently stored for each display on a single display screen such as explanatory slide No. 1. The selection thus can be made for each slide to determine the display order of the slides.

Furthermore, since the explanatory slide and the literature slide can be associated with each other for each slide arbitrarily, the system is extremely easy to use for the user such as MR who carries out the aforementioned operation by the tablet terminal 20.

In particular, even the MR who does not have an intimate knowledge of PDF format of slides or the like can readily perform the operation.

Figure 10:
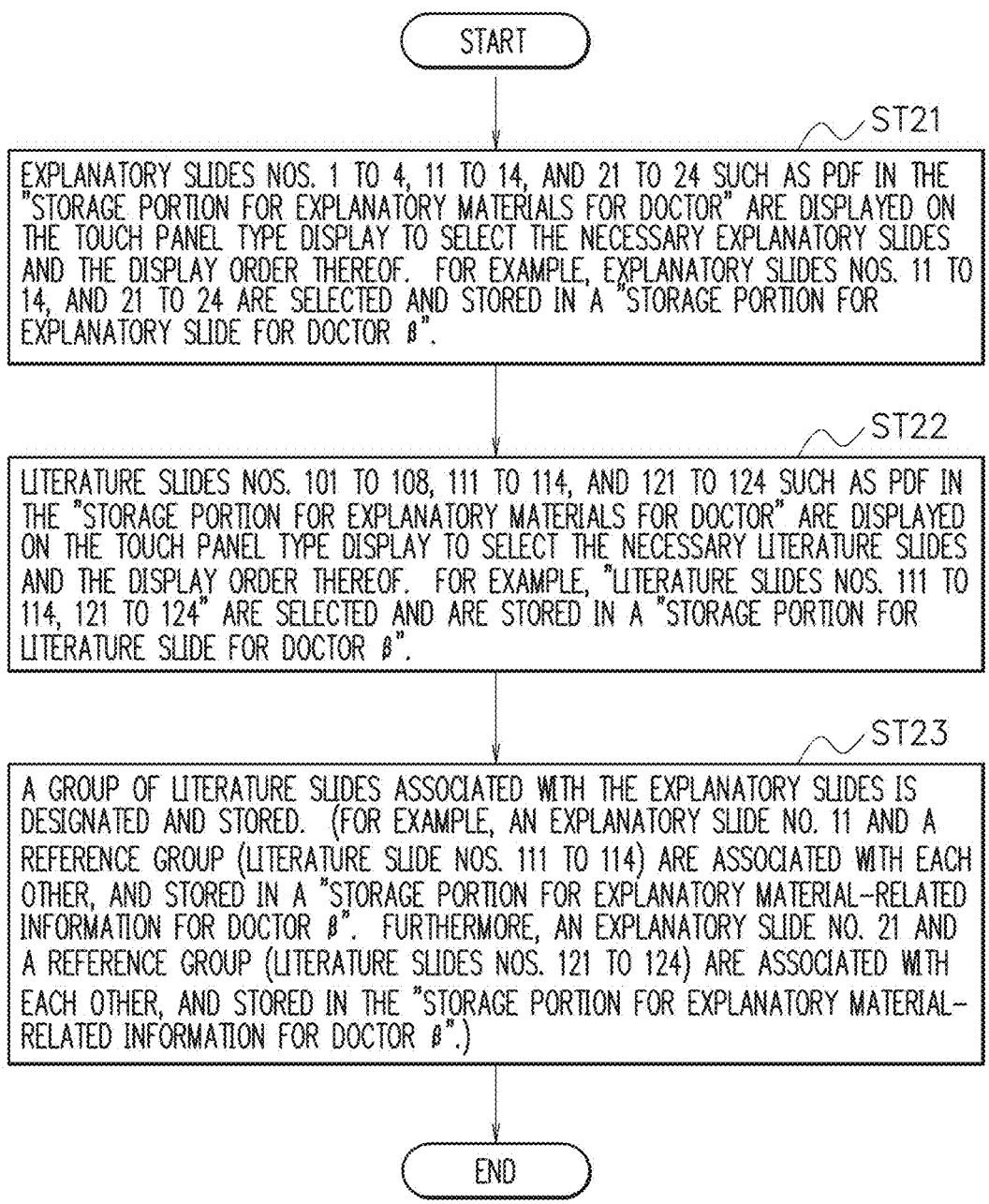
FIG. 10 is another schematic flow chart showing an operational example of the managing system of explanatory materials for doctor.

FIG. 10 is a schematic flow chart showing the steps of creating explanatory materials for doctor dedicated to the doctor β.

The MR executes at the steps in FIG. 10 the preparation of slides for the explanation shown in FIG. 7.

First, at ST21, explanatory slides Nos. 1 to 4, 11 to 14, and 21 to 24 such as PDF in the storage portion for explanatory materials for doctor 31 in FIG. 4 are displayed on the touch panel type display 21 to select the necessary explanatory slides and the display order thereof.

For example, Explanatory Slides Nos. 11 to 14, and 21 to 24 are selected to be displayed in this order, and stored in a "storage portion for explanatory slide for doctor β 35".

Then, the procedure proceeds to ST22. At ST22, Literature Slides Nos. 101 to 108, 111 to 114, and 121 to 124 such as PDF in the storage portion for explanatory materials for doctor 31 are displayed on the touch panel type display 21 to select the necessary literature slides and the display order thereof.

For example, "Literature Slides Nos. 111 to 114, 121 to 124" which are to be used in FIG. 7 are selected to be displayed in this order, and are stored in a "storage portion for literature slide for doctor β 36".

Then, the procedure proceeds to ST23. At ST23, a group of literature slides associated with the explanatory slides is designated and stored.

For example, an explanatory slide No. 11 and a reference group (literature slide Nos. 111 to 114) are associated with each other, and stored in a "storage portion for explanatory material-related information for doctor β 37". Furthermore, an explanatory slide No. 21 and a reference group (literature slides Nos. 121 to 124) are associated with each other, and stored in the storage portion for explanatory material-related information for doctor β 37.

In this manner, in the present embodiment, if the explanatory slides for the doctor α and the literature slides associated therewith are different from the explanatory slide for the doctor β and the literature slide associated therewith, it is not necessary to create separate slide sets respectively as in a conventional case. One explanatory slide and one literature slide can be utilized as slides for both the doctors, respectively.

Therefore, it is possible to reduce the amount of data to be stored in the tablet terminal 20 compared with the conventional case.

Figure 11:
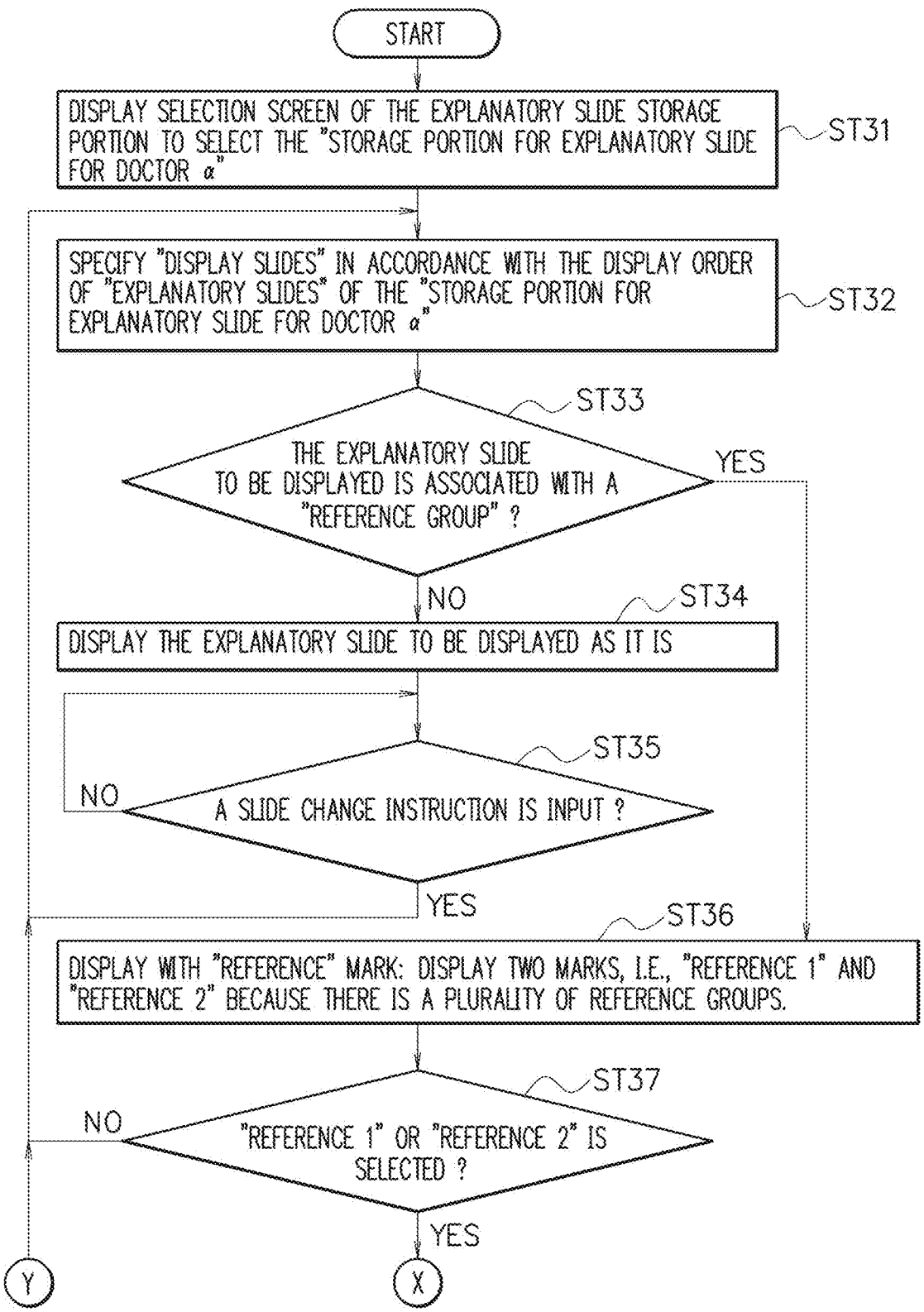
FIG. 11 is another schematic flow chart showing an operational example of the managing system of explanatory materials for doctor.
Figure 12:
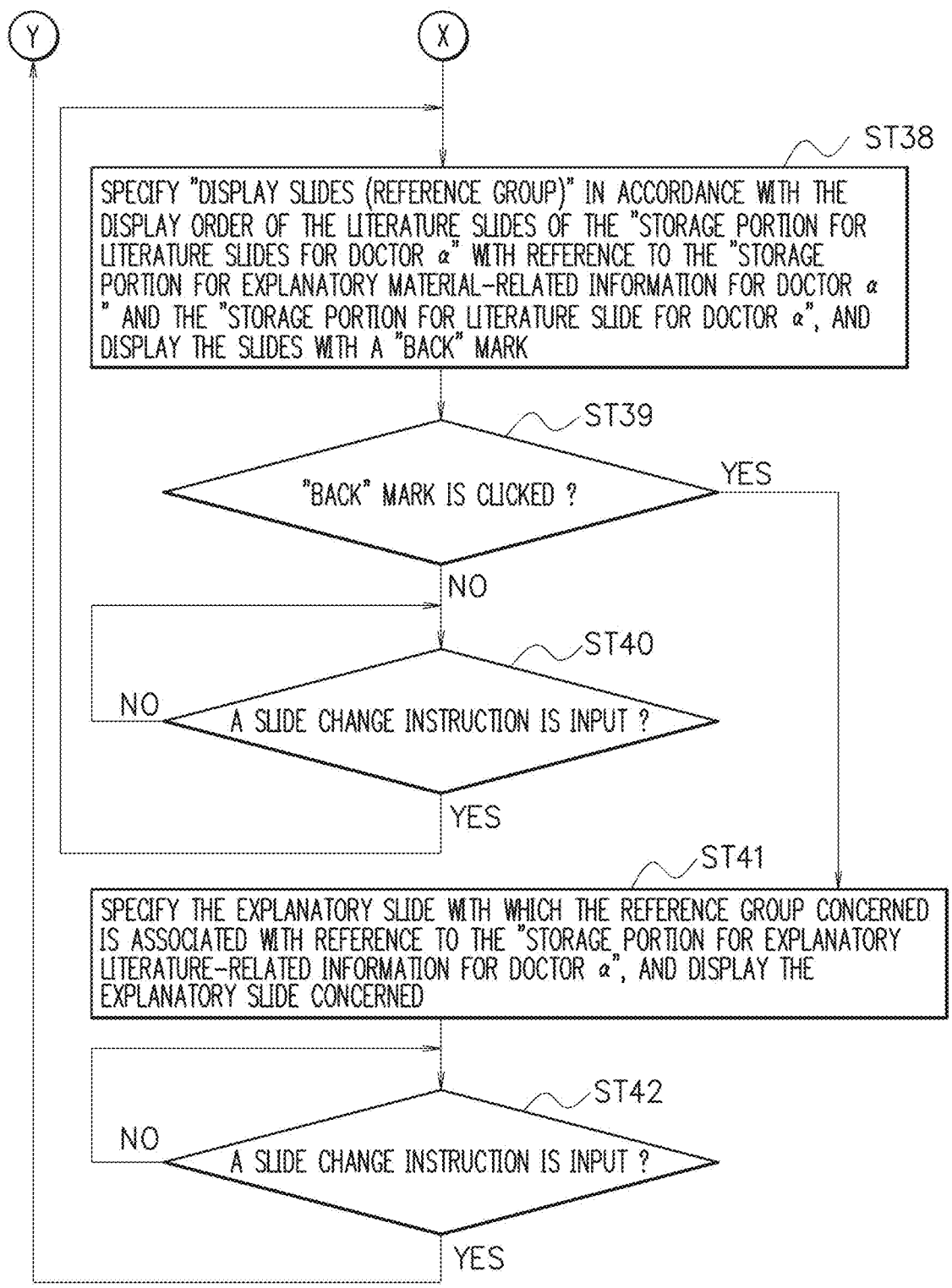
FIG. 12 is another schematic flow chart showing an operational example of the managing system of explanatory materials for doctor.

FIGS. 11 and 12 are schematic flow charts showing the steps of displaying slides shown in FIG. 6 on the tablet terminal 20 while meeting with the doctor α.

In addition, the display of slides in FIG. 7 for the explanation to the doctor β is almost the same as that in the case of the doctor α, and the explanation thereof will be omitted.

First, the MR turns on his/her tablet terminal 20. Then, at ST31, a selection screen of the explanatory slide storage portion is displayed on the touch panel type display 21, and the MR operates it to select the "storage portion for explanatory slide for doctor α 32".

Then, the procedure proceeds to ST32. At ST32, a "display slide specifying portion (program) 41" in FIG. 5 is activated to specify "display slides" in accordance with the display order of "Explanatory Slides" of the "storage portion for explanatory slide for doctor α 32".

Specifically, as shown in FIG. 6, "Explanatory Slide No. 1" is displayed on the touch panel type display 21.

Then, the procedure proceeds to ST33. At ST33, a "relevant information determining portion (program) 42" in FIG. 5 is activated to determine whether or not the explanatory slide to be displayed is associated with a "reference group".

Specifically, the determination is made with reference to the storage portion for explanatory material-related information for doctor α 34 in FIG. 4.

No display group is associated with "Slide No. 1", and thus the procedure proceeds to ST34.

At ST34, the explanatory slide to be displayed is displayed as it is.

Then, the procedure proceeds to ST35. At ST35, it is determined whether or not a slide change instruction is input via the touch panel type display 21. If the instruction is input, the procedure proceeds to ST32 to display "Explanatory Slide No. 2" as shown in FIG. 6.

In this manner, if "Explanatory Slide No. 3" is displayed, it is determined at ST33 that a "reference group" is associated therewith, and then procedure proceeds to ST36.

At ST36, as shown in FIG. 6, a mark of "Reference 1" corresponding to a reference group 1 and that of "Reference 2" corresponding to a reference group 2 are displayed on "Explanatory Slide No. 3".

Then, the procedure proceeds to ST37. At ST37, it is determined whether or not the MR touches and clicks "Reference 1" or "Reference 2" on the "Explanatory Slide No. 3".

At ST37, when "Reference 1" is clicked, for example, the procedure proceeds to ST38 in FIG. 12.

At ST38, a "literature slide display portion (program) 43" in FIG. 5 is activated to specify "display slides (reference group 1 (literature slides Nos. 105 to 108, 111, 112, 121))" in accordance with the display order of the literature slides of the "storage portion for literature slides for doctor α 33" with reference to the "storage portion for explanatory material-related information for doctor α 34" and the "storage portion for literature slide for doctor α 33", and display the slides with a "BACK" mark.

More specifically, as shown in FIG. 6, "Literature Slide No. 105" is displayed at first, and the "BACK" mark is displayed at the same time.

Then, the procedure proceeds to ST39. At ST39, it is determined whether or not the "BACK" mark is touched and clicked. If it is determined at ST39 the "BACK" mark is not clicked, the procedure proceeds to ST40.

At ST40, it is determined whether or not a slide change instruction is input. If the slide change instruction is input from the touch panel type display 21, the procedure proceeds to ST38 to display the next "literature Slide No. 106" in FIG. 6 is displayed with the "BACK" mark.

In this manner, if the literature slides are displayed in sequence, "Literature Slide No. 108" in FIG. 6 is displayed with the "BACK" mark, and the "BACK" mark is clicked at ST39, the procedure proceeds to ST41.

At ST39 and ST41, a "BACK mark execution portion (program) 44" in FIG. 5 is executed. If it is determined that a "BACK" mark is clicked, "Explanatory Slide No. 3" is specified which is the explanatory slide with which the reference group concerned, i.e., the reference group 1 in the aforesaid example, is associated, with reference to the explanatory literature-related information storage portion for doctor α 34. In the next screen, "Explanatory Slide No. 3" which is the explanatory slide concerned is displayed on the touch panel type display 21.

Therefore, even if the MR explains "Literature Slide No. 105" to "Literature Slide No. 108" which are the relevant literatures while explaining "Explanatory Slide No. 3", it is possible to promptly return to "Explanatory Slide No. 3" in the next screen only by clicking the "BACK" mark of "Literature Slide No. 108".

Consequently, it is possible to prevent the occurrence of adverse effect as in the conventional case, i.e., it takes time to transfer from the literature slide to the explanatory slide, so that the explanation by the MR is interrupted resulting in decrease in the effect of explanation.

More specifically, it is possible to promptly return the screen from the explanation of the literature slide to the previous explanatory slide screen. It is possible to return to the previous explanatory slide in regard to any of "Literature Slide No. 105" to "Literature Slide No. 108" in FIG. 6.

Consequently, the MR can promptly return to the previous explanatory slide, i.e., "Explanatory Slide No. 3" at any time by clicking the "BACK" mark at an arbitrary timing while seeing the response of the doctor α.

Furthermore, as shown in FIG. 6, a plurality of reference groups can be associated with a single "Explanatory Slide No. 3" to form a "Reference" mark for transferring to each group.

In this case, the MR can select any of desirable one as appropriate by seeing the response of the doctor to be explained.

Furthermore, in contrast to the present embodiment, it is possible to configure that, if the selected "Reference" mark, e.g., the mark of "Reference 2", is selected, such a fact is stored, and, in order to preferentially display the literature slide of "Reference 2" next time, "Reference 2" is changed to "Reference 1" so that the fact concerned is notified to the MR.

The procedure proceeds from ST41 to ST42. At ST42, "Explanatory Slide No. 4" which is the explanatory slide following "Explanatory Slide No. 3" in FIG. 6 is displayed on the touch panel type display 21.

In this manner, all the explanatory slides in FIG. 6 to Explanatory Slide No. 21 are displayed, the explanation by the MR to the doctor α is finished.

Furthermore, the explanation in FIG. 7 to the doctor β is performed in the same manner.

In addition, the present invention is not limited to the embodiments described above. For example, it is possible to apply the present invention to the explanation of "presentation of materials and simulation along with opening a new store", etc., not for the MR.

More specifically, it is possible to display a detailed simulation screen (data of cash and deposits of a customer or the like) as a literature slide relative to an explanatory slide of specific regional characteristics, simulation of customer attraction, and simulation of store planning and borrowing funds.

Explanations of the explanatory slides and literature slides are described here. FIG. 13A shows one example of the explanatory slide. The explanatory slide has three reference groups that are related to the slide. These groups are displayed with three reference marks that are "1st Reference," "2nd Reference" and "3rd Reference." These marks are denoted with XR1 to XR3 in the drawing. When more than one reference group are related to one explanatory side, the slide may be named as a single explanatory slide. A back mark (XB), and a next mark (XN) are disposed at a lower right in the screen. When the back mark in the explanatory slide is clicked, it proceeds to the previous explanatory slide in accordance with the display order that is previously registered for the doctor, and the previous explanatory slide is displayed. In the similar fashion, when the next mark in the explanatory slide is clicked, it proceeds to the next explanatory slide in accordance with the display order that is previously registered for the doctor, and the next explanatory slide is displayed.

A plurality of reference marks (XR1~XR3) of the reference groups is placed at fixed positions in the slide. The listing order also is fixed. The positions and the orders, however, may be changeable. For example, when "2nd Reference" mark is clicked in the explanatory slide (or the parent slide, or corresponding explanatory slide) and one of the literature slides related to the 2nd Reference group is displayed, it is understood that the doctor has an interest in the contents of the reference group or some of the literature slides are important for the doctor. Accordingly, when the parent slide is displayed later, "2nd Reference" mark moves up (or ascends) and is placed at the top row, "1st Reference" mark descents to the second row by exchanging their positions of "2nd Reference" mark (XR2) with that of "1st Reference" mark (XR1). "3rd Reference" mark remains at the same position (or third row). Namely, the new order of the reference marks becomes XR2-XR1-RX3. In a case where literature slides of the first and second reference groups were displayed but any literature slide of the third reference group has not been displayed, the third reference mark (XR3) may move up to the top row. With the configuration, the user (operator) easily find which reference group has not been explained.

In the embodiment in FIG. 13A, the reference marks are aligned in a top-down direction. The direction is not limited to the top-down direction (or vertical direction). These marks may be arranged in the horizontal direction wherein the left position means the top and the right position means the bottom, or vice versa. The ascending/descending order may be either vertical or horizontal. Also, the reference marks displayed in an exemplary slide may each has different appearances from others, or all the reference marks may be the same appearance. The appearances are formed with symbol, number, text, color, or shape.

Even though reference marks are always displayed in the same manner, it is possible to link one reference mark with a different reference group by switching a relation between the reference groups and the reference marks. Accordingly, the user finds a different reference group to be displayed when clicking the same reference mark twice.

Figure 13B:
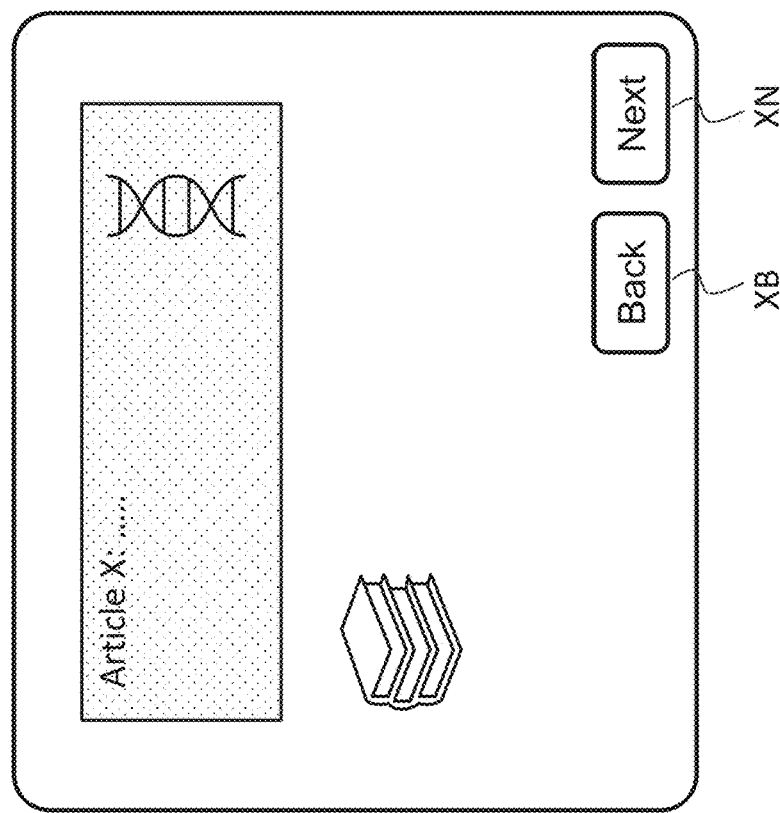
[FIGS. 13A, 13B]
Figure 13A:
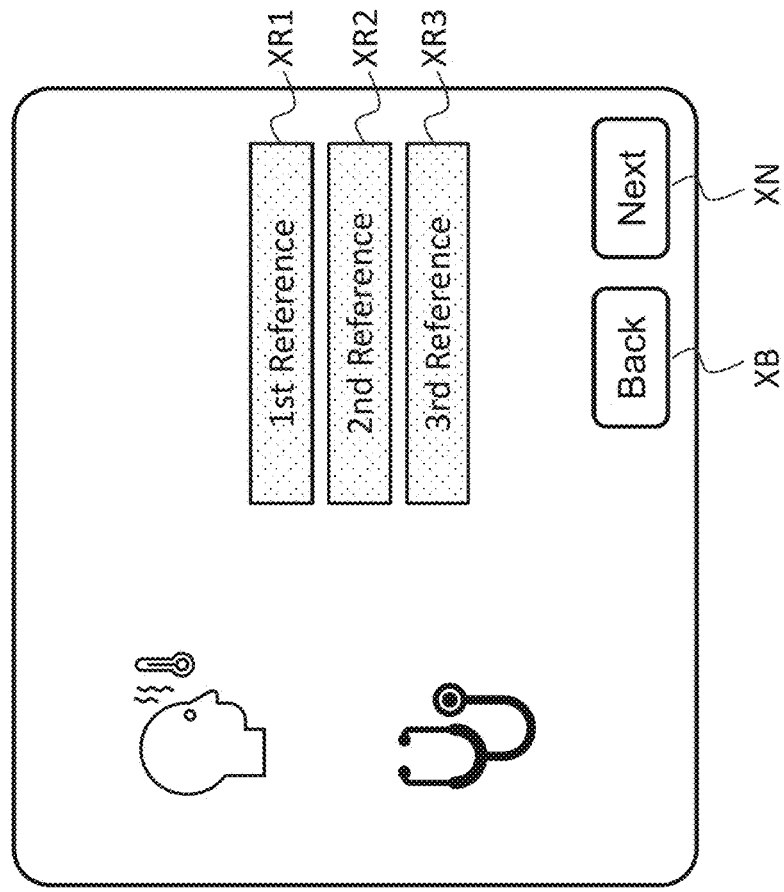

FIG. 13B is one example of the literature slide. These are a back mark (XB), "Back," and a next mark (XN), "Next," displayed at the lower right in the screen. As a preferred embodiment, the back mark and the next mark are placed at the same position as in the explanatory slide and have the same appearance as in the explanatory slide in FIG. 13A. By displaying these marks in the fixed position and with the fixed appearance, it is possible to provide a user-friendly interface to the users When the next mark in the literature slide is clicked, it proceeds to the next literature slide in accordance with the display order that is previously registered for the doctor, and the next literature slide is displayed. On the other hand, when the back mark in the literature slide is clicked, it does not proceed to the previous literature slide in accordance with the display order. In the invention, it proceeds to the parent slide and the parent slide is displayed. The parent slide (or the corresponding explanatory slide) means one explanatory slide on which the reference mark of the literature slide is displayed. All literature slides belonging to one reference group are defined as child slides. Referring to FIG. 6, explanatory slide No. 3 displaying two reference marks that are Reference 1 and Reference 2 is a parent slide (or the corresponding explanatory slide). Literature slides (Nos. 105-108) belonging to 1st reference group with "Reference 1" and literature slides (Nos. 101-104) belonging to 2nd reference group with "Reference 2" are child slides. Whenever the back mark in any of the child slide is clicked, it always proceeds to the parent slide, displaying it at the next slide.

In the specification, the claims and the drawings, reference marks, back marks and next marks are described. When this invention is embodied, these marks are not limited to these wordings. Regardless of languages, when a mark indicates to the user to move to the next slide, the mark is recognized as the next mark. When a mark indicates to the user to move back to the previous side or back to the parent slide, the mark is recognized in the back mark. Additionally, any shapes or symbols are available for the back and next marks such as arrows. For the reference marks, not only "Reference" or "Ref." but also any text, symbol, and shapes that conveys an idea to provide further information related to the parent slide are available. Also, in the specification, the "click" means any action by the user (operator) that inputs an instruction to a computer.

EXPLANATION OF REFERENCE NUMERALS

1 . . . Managing system of explanatory materials for doctor,
4 . . . Pharmaceutical company,
10 . . . Management server,
11 . . . Database of explanatory materials for doctor,
12 . . . Server controller,
13 . . . Server side communication device,
14 . . . Server side display,
15 . . . Server side input device,
20 . . . Tablet terminal,
21 . . . Touch panel type display,
22 . . . Input button,
23 . . . Terminal controller,
24 . . . Terminal side communication device,
30 . . . First various information storage portion,
31 . . . Storage portion for explanatory materials for doctor,
32 . . . Storage portion for explanatory slide for doctor α,
33 . . . Storage portion for literature slide for doctor α,
34 . . . Storage portion for explanatory material-related information for doctor α,
35 . . . Storage portion for explanatory slide for doctor,
36 . . . Storage portion for literature slide for doctor β,
37 . . . Storage portion for explanatory material-related information for doctor,
40 . . . Second various information storage portion,
41 . . . Display slide specifying portion (program),
42 . . . Relevant information determining portion (program),
43 . . . Literature slide display portion (program),
44 . . . BACK mark execution portion (program).

The invention claimed is:

1. A managing system of explanatory materials for doctors comprising:
a management server managing slide information as being explanatory materials for doctors, and
a mobile terminal device being held by a medical representative configured to be able to communicate with the management server, the mobile terminal device, comprising a display displaying various information, wherein:
the slide information to be displayed on the display of the mobile terminal includes a plurality of pieces of the slide information independently stored as the slide information,
the pieces of the slide information being configured to be able to be combined arbitrarily,
the pieces of the slide information further composing main explanatory slide information and literature slide information wherein
the main explanatory slide information is used in a main explanation, being composed with a plurality of explanatory slides and slide numbers of the explanatory slides wherein each of the explanatory slides is assigned with one of the slide numbers that is different from other explanatory slides, and
the literature slide information is used to provide more detailed information that is in relation to the main explanatory slide information, being composed with a plurality of literature slides and slide numbers of the literature slides wherein each of the literature slides is assigned with one of the slide numbers that is different from other literature slides, and
a display order of the explanatory slides is predetermined following the slide numbers of the explanatory slides and stored in a storage portion for explanatory slide in a data storage device, and a display order of the literature slides is predetermined following the slide numbers of the literature slides and stored in a slide storage portion of the data storage device,
reference groups are formed, in each of which one or more of the literature slides are contained wherein each of the literature slides is displayed with only one "Back" mark, and all the "Back" marks in the literature slides have a same appearance and are positioned at a same location in the literature slides, and some of the explanatory slides are associated with one or more of the reference groups, these reference groups are stored in a storage portion for explanatory material-related information of the data storage device, further at least one reference group contains three or more of the literature slides, and when the one reference group is associated with one explanatory slide, the one reference group is regarded as an associated reference group and the one explanatory slide is regarded as a corresponding explanatory slide, when the corresponding explanatory slide is displayed on the display in the display order, a relevant information determining portion in the data storage device operates and "Reference" mark of the associated reference group is displayed on the corresponding explanatory slide wherein the explanatory slides are displayed one slide by one slide following the display order of the explanatory slides in correspondence with an action, which is executed by the medical representative, for moving to the next explanatory slide until one of the "Reference" marks is clicked, when the "Reference" mark of the associated reference group is clicked while the corresponding explanatory slide is displayed, a slide display portion in the data storage device operates to read all the literature slides contained in the associated reference group, displaying the literature slides one slide by one slide following the display order of the literature slides, the "Back" marks in the literature slides contained in the associated reference group are displayed only when the "Reference" mark of the associated reference group is clicked to display the literature slides, and whenever the "Back" mark is clicked on any of the literature slides in the associated reference group, a Back mark execution portion in the data storage device operates, and the display is configured to jump to the corresponding explanatory slide with the "Reference" mark being displayed previously, skipping the literature slides having being displayed previously only by a single action of clicking the "Back" mark, when two of the reference groups, each of which includes the associated reference group, is associated with a single explanatory slide, and at least two of the "Reference" marks are formed for transferring to each of the reference groups, a reference number is assigned in each of the "Reference" marks wherein the reference number indicates a priority order to be displayed, when one of the "Reference" marks, which is positioned below the other of the "Reference" mark in the single explanatory slide, is clicked, the reference number of the clicked "Reference" mark is raised in the main explanatory slide information in the next time such that the one of the "Reference" marks is displayed above the other of the "Reference" mark in the single explanatory slide, and the main explanatory slide information and the literature slide information are composed to be displayed in the PDF ("Portable Document Format") format.

2. The managing system of explanatory materials according to claim 1, wherein the explanatory slides and the literature slides each have "Next" marks, when any of the "Next" marks in the explanatory slides is clicked, the managing system moves to the next explanatory slide in accordance with the display order of the explanatory slides, when any of the "Next" marks in the literature slides is clicked, the managing system moves to the next literature slide in accordance with the display order of the literature slides, and the "Next" marks in the explanatory slides have a same appearance and a same location as the "Next" marks in the literature slides.

* * * * *